(12) United States Patent
Sartor et al.

(10) Patent No.: US 7,955,327 B2
(45) Date of Patent: *Jun. 7, 2011

(54) MOTION DETECTOR FOR CONTROLLING ELECTROSURGICAL OUTPUT

(75) Inventors: Joe D. Sartor, Longmont, CO (US); Dale F. Schmaltz, Fort Collins, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1186 days.

This patent is subject to a terminal disclaimer.

(21) Appl. No.: 11/651,385

(22) Filed: Jan. 8, 2007

(65) Prior Publication Data

US 2007/0142832 A1 Jun. 21, 2007

Related U.S. Application Data

(63) Continuation of application No. 10/781,084, filed on Feb. 17, 2004, now Pat. No. 7,235,072.

(60) Provisional application No. 60/448,520, filed on Feb. 20, 2003, provisional application No. 60/533,695, filed on Jan. 1, 2004.

(51) Int. Cl.
*A61B 18/14* (2006.01)

(52) U.S. Cl. .............................. 606/45; 606/34; 606/41

(58) Field of Classification Search .......... 606/1, 32–35, 606/41, 45–50

See application file for complete search history.

(56) References Cited

U.S. PATENT DOCUMENTS

| | | |
|---|---|---|
| 2,031,682 A | 2/1936 | Frederick et al. |
| 2,102,270 A | 12/1937 | Hyams |
| 2,993,178 A | 7/1961 | Burger |
| 3,058,470 A | 10/1962 | Seeliger et al. |
| 3,219,029 A | 11/1965 | Richards et al. |
| 3,460,539 A | 8/1969 | Anhalt, Sr. |
| 3,494,363 A | 2/1970 | Jackson |
| 3,648,001 A | 3/1972 | Anderson et al. |
| 3,675,655 A | 7/1972 | Sittner |
| 3,699,967 A | 10/1972 | Anderson |
| 3,720,896 A | 3/1973 | Beierlein |
| 3,801,766 A | 4/1974 | Morrison, Jr. |
| 3,801,800 A | 4/1974 | Newton |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |

(Continued)

FOREIGN PATENT DOCUMENTS

DE 24 29 021 A1 1/1976

(Continued)

OTHER PUBLICATIONS

International Search Report from PCT/US03/37111; Jul. 21, 2004.

(Continued)

*Primary Examiner* — Michael Peffley

(57) ABSTRACT

An electrosurgical instrument having a movement sensing device for controlling the electrosurgical output thereof, is disclosed. In one aspect of the present disclosure, the electrosurgical instrument includes an elongated housing, an electrically conductive element supported within the housing and extending distally from the housing, the electrically conductive element connectable to a source of electrosurgical energy, and a sensor disposed within the housing and in electrical connection with the electrosurgical generator. The sensor detects movement of the electrically conductive element and communicates a signal to the electrosurgical generator relating to the movement of the electrically conductive element. The source of electrosurgical energy supplies electrosurgical energy in response to the signal from the sensor.

10 Claims, 4 Drawing Sheets

U.S. PATENT DOCUMENTS

| | | |
|---|---|---|
| 3,906,955 A | 9/1975 | Roberts |
| 3,911,241 A | 10/1975 | Jarrard |
| 3,967,084 A | 6/1976 | Pounds |
| 3,974,833 A | 8/1976 | Durden, III |
| 4,014,343 A | 3/1977 | Esty |
| 4,032,738 A | 6/1977 | Esty et al. |
| 4,034,761 A | 7/1977 | Prater et al. |
| 4,038,984 A | 8/1977 | Sittner |
| 4,112,950 A | 9/1978 | Pike |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |
| 4,492,832 A | 1/1985 | Taylor |
| 4,545,375 A | 10/1985 | Cline |
| 4,562,838 A | 1/1986 | Walker |
| 4,589,411 A | 5/1986 | Friedman |
| 4,593,691 A | 6/1986 | Lindstrom et al. |
| 4,595,809 A | 6/1986 | Pool |
| 4,606,342 A | 8/1986 | Zamba et al. |
| 4,619,258 A | 10/1986 | Pool |
| 4,620,548 A | 11/1986 | Hasselbrack |
| 4,625,723 A | 12/1986 | Altnether et al. |
| 4,640,279 A | 2/1987 | Beard |
| 4,642,128 A | 2/1987 | Solorzano |
| 4,644,950 A * | 2/1987 | Valli ............................... 606/46 |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,712,544 A | 12/1987 | Ensslin |
| 4,735,603 A | 4/1988 | Goodson et al. |
| 4,754,754 A | 7/1988 | Garito et al. |
| 4,781,175 A * | 11/1988 | McGreevy et al. ............. 606/40 |
| 4,785,807 A | 11/1988 | Blanch |
| 4,788,977 A | 12/1988 | Farin et al. |
| 4,794,215 A | 12/1988 | Sawada et al. |
| 4,796,623 A | 1/1989 | Krasner et al. |
| 4,803,323 A | 2/1989 | Bauer et al. |
| 4,811,733 A | 3/1989 | Borsanyi et al. |
| 4,827,911 A | 5/1989 | Broadwin et al. |
| 4,827,927 A | 5/1989 | Newton |
| D301,739 S | 6/1989 | Turner et al. |
| 4,846,790 A | 7/1989 | Hornlein et al. |
| 4,850,353 A | 7/1989 | Stasz et al. |
| 4,860,745 A | 8/1989 | Farin et al. |
| 4,862,889 A | 9/1989 | Feucht |
| 4,862,890 A | 9/1989 | Stasz et al. |
| 4,869,715 A | 9/1989 | Sherburne |
| 4,872,454 A | 10/1989 | DeOliveira et al. |
| 4,876,110 A | 10/1989 | Blanch |
| 4,886,060 A | 12/1989 | Wiksell |
| 4,901,719 A | 2/1990 | Trenconsky et al. |
| 4,903,696 A | 2/1990 | Stasz et al. |
| 4,909,249 A | 3/1990 | Akkas et al. |
| 4,911,159 A | 3/1990 | Johnson et al. |
| 4,916,275 A | 4/1990 | Almond |
| 4,919,129 A | 4/1990 | Weber, Jr. et al. |
| 4,921,476 A | 5/1990 | Wuchinich |
| 4,922,903 A | 5/1990 | Welch et al. |
| 4,931,047 A | 6/1990 | Broadwin et al. |
| 4,949,734 A | 8/1990 | Bernstein |
| 4,969,885 A | 11/1990 | Farin |
| 4,986,839 A | 1/1991 | Wertz et al. |
| 4,988,334 A | 1/1991 | Hornlein et al. |
| 5,000,754 A | 3/1991 | DeOliveira et al. |
| 5,011,483 A | 4/1991 | Sleister |
| 5,013,312 A | 5/1991 | Parins et al. |
| 5,015,227 A | 5/1991 | Broadwin et al. |
| 5,026,368 A | 6/1991 | Adair |
| 5,035,695 A | 7/1991 | Weber, Jr. et al. |
| 5,035,696 A | 7/1991 | Rydell |
| 5,046,506 A | 9/1991 | Singer |
| 5,055,100 A | 10/1991 | Olsen |
| 5,071,418 A | 12/1991 | Rosenbaum |
| 5,074,863 A | 12/1991 | Dines |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,108,391 A | 4/1992 | Flachenecker et al. |
| 5,133,714 A | 7/1992 | Beane |
| 5,147,292 A | 9/1992 | Kullas et al. |
| D330,253 S | 10/1992 | Burek |
| 5,154,709 A | 10/1992 | Johnson |
| 5,160,334 A | 11/1992 | Billings et al. |
| 5,162,044 A | 11/1992 | Gahn et al. |
| 5,167,659 A | 12/1992 | Ohtomo et al. |
| 5,178,012 A | 1/1993 | Culp |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,234,429 A | 8/1993 | Goldhaber |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,261,906 A | 11/1993 | Pennino et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,312,400 A | 5/1994 | Bales et al. |
| 5,312,401 A | 5/1994 | Newton et al. |
| 5,318,516 A | 6/1994 | Cosmescu |
| 5,318,565 A | 6/1994 | Kuriloff et al. |
| 5,322,503 A | 6/1994 | Desai |
| 5,330,470 A | 7/1994 | Hagen |
| 5,334,183 A | 8/1994 | Wuchinich |
| 5,342,356 A | 8/1994 | Ellman et al. |
| 5,348,555 A | 9/1994 | Zinnanti |
| 5,366,464 A | 11/1994 | Belknap |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,423,838 S | 6/1995 | Willard |
| 5,431,645 A | 7/1995 | Smith et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,468,240 A | 11/1995 | Gentelia et al. |
| 5,472,442 A | 12/1995 | Klicek |
| 5,472,443 A | 12/1995 | Cordis et al. |
| 5,484,398 A | 1/1996 | Stoddard |
| 5,484,434 A | 1/1996 | Cartmell et al. |
| 5,486,162 A | 1/1996 | Brumbach |
| 5,496,314 A | 3/1996 | Eggers |
| 5,498,654 A | 3/1996 | Shimasaki et al. |
| D370,731 S | 6/1996 | Corace et al. |
| 5,531,722 A | 7/1996 | Van Hale |

| Patent No. | Date | Inventor(s) | Patent No. | Date | Inventor(s) |
|---|---|---|---|---|---|
| 5,549,604 A | 8/1996 | Sutcu et al. | 6,200,311 B1 | 3/2001 | Danek et al. |
| 5,561,278 A | 10/1996 | Rutten | D441,077 S | 4/2001 | Garito et al. |
| 5,601,224 A | 2/1997 | Bishop et al. | 6,213,999 B1 | 4/2001 | Platt, Jr. et al. |
| 5,609,573 A | 3/1997 | Sandock | 6,214,003 B1 | 4/2001 | Morgan et al. |
| 5,626,575 A | 5/1997 | Crenner | 6,238,388 B1 | 5/2001 | Ellman et al. |
| 5,630,417 A | 5/1997 | Petersen et al. | 6,241,723 B1 | 6/2001 | Heim et al. |
| 5,630,426 A | 5/1997 | Eggers et al. | 6,241,753 B1 | 6/2001 | Knowlton |
| 5,630,812 A | 5/1997 | Ellman et al. | 6,249,706 B1 * | 6/2001 | Sobota et al. ................. 607/115 |
| 5,633,578 A | 5/1997 | Eggers et al. | 6,251,110 B1 | 6/2001 | Wampler |
| 5,634,912 A | 6/1997 | Injev | 6,257,241 B1 | 7/2001 | Wampler |
| 5,634,935 A | 6/1997 | Taheri | 6,258,088 B1 | 7/2001 | Tzonev et al. |
| 5,643,256 A | 7/1997 | Urueta | 6,273,862 B1 | 8/2001 | Privitera et al. |
| D384,148 S | 9/1997 | Monson | 6,277,083 B1 | 8/2001 | Eggers et al. |
| 5,669,907 A | 9/1997 | Platt, Jr. et al. | 6,286,512 B1 | 9/2001 | Loeb et al. |
| 5,674,219 A | 10/1997 | Monson et al. | 6,287,305 B1 | 9/2001 | Heim et al. |
| 5,693,044 A | 12/1997 | Cosmescu | 6,287,344 B1 | 9/2001 | Wampler et al. |
| 5,693,050 A | 12/1997 | Speiser | 6,312,441 B1 | 11/2001 | Deng |
| 5,693,052 A | 12/1997 | Weaver | 6,325,799 B1 | 12/2001 | Goble |
| 5,697,926 A | 12/1997 | Weaver | D453,222 S | 1/2002 | Garito et al. |
| 5,702,360 A | 12/1997 | Dieras et al. | D453,833 S | 2/2002 | Hess |
| 5,702,387 A | 12/1997 | Arts et al. | 6,350,276 B1 | 2/2002 | Knowlton |
| 5,712,543 A | 1/1998 | Sjostrom | 6,352,544 B1 | 3/2002 | Spitz |
| 5,713,895 A | 2/1998 | Lontine et al. | 6,355,034 B2 | 3/2002 | Cosmescu |
| 5,720,745 A | 2/1998 | Farin et al. | 6,358,281 B1 | 3/2002 | Berrang et al. |
| D393,067 S | 3/1998 | Geary et al. | 6,361,532 B1 | 3/2002 | Burek |
| 5,749,869 A | 5/1998 | Lindenmeier et al. | D457,955 S | 5/2002 | Bilitz |
| 5,765,418 A | 6/1998 | Rosenberg | 6,386,032 B1 | 5/2002 | Lemkin et al. |
| 5,776,092 A | 7/1998 | Farin et al. | 6,395,001 B1 | 5/2002 | Ellman et al. |
| 5,788,688 A | 8/1998 | Bauer et al. | 6,402,741 B1 | 6/2002 | Keppel et al. |
| 5,797,907 A | 8/1998 | Clement | 6,402,742 B1 | 6/2002 | Blewett et al. |
| 5,800,431 A | 9/1998 | Brown | 6,402,743 B1 | 6/2002 | Orszulak et al. |
| 5,836,897 A | 11/1998 | Sakurai et al. | 6,402,748 B1 | 6/2002 | Schoenman et al. |
| 5,836,909 A | 11/1998 | Cosmescu | 6,409,725 B1 | 6/2002 | Khandkar et al. |
| 5,836,944 A | 11/1998 | Cosmescu | 6,413,255 B1 | 7/2002 | Stern |
| D402,030 S | 12/1998 | Roberts et al. | 6,416,491 B1 | 7/2002 | Edwards et al. |
| D402,031 S | 12/1998 | Roberts et al. | 6,416,509 B1 | 7/2002 | Goble et al. |
| 5,843,109 A | 12/1998 | Mehta et al. | 6,425,912 B1 | 7/2002 | Knowlton |
| 5,846,236 A | 12/1998 | Lindenmeier et al. | 6,458,122 B1 | 10/2002 | Pozzato |
| 5,859,527 A | 1/1999 | Cook | 6,458,125 B1 | 10/2002 | Cosmescu |
| 5,868,768 A | 2/1999 | Wicherski et al. | 6,461,352 B2 | 10/2002 | Morgan et al. |
| 5,876,400 A | 3/1999 | Songer | 6,464,702 B2 | 10/2002 | Schulze et al. |
| 5,888,200 A | 3/1999 | Walen | 6,471,659 B2 | 10/2002 | Eggers et al. |
| 5,893,848 A * | 4/1999 | Negus et al. ................. 606/41 | 6,494,882 B1 * | 12/2002 | Lebouitz et al. ................. 606/45 |
| 5,893,849 A | 4/1999 | Weaver | 6,500,169 B1 | 12/2002 | Deng |
| 5,893,862 A | 4/1999 | Pratt et al. | 6,511,479 B2 | 1/2003 | Gentelia et al. |
| 5,913,864 A | 6/1999 | Garito et al. | 6,526,320 B2 | 2/2003 | Mitchell |
| 5,919,219 A | 7/1999 | Knowlton | 6,551,313 B1 | 4/2003 | Levin |
| 5,928,159 A | 7/1999 | Eggers et al. | 6,558,383 B2 | 5/2003 | Cunningham et al. |
| 5,938,589 A | 8/1999 | Wako et al. | 6,585,664 B2 | 7/2003 | Burdorff et al. |
| 5,941,887 A | 8/1999 | Steen et al. | 6,589,239 B2 | 7/2003 | Khandkar et al. |
| 5,944,737 A | 8/1999 | Tsonton et al. | 6,610,054 B1 | 8/2003 | Edwards et al. |
| 5,951,548 A | 9/1999 | DeSisto et al. | 6,610,057 B1 | 8/2003 | Ellman et al. |
| 5,951,581 A | 9/1999 | Saadat et al. | 6,616,658 B2 | 9/2003 | Ineson |
| 5,954,686 A | 9/1999 | Garito et al. | 6,618,626 B2 | 9/2003 | West, Jr. et al. |
| 5,972,007 A | 10/1999 | Sheffield et al. | 6,620,161 B2 | 9/2003 | Schulze et al. |
| 6,004,318 A | 12/1999 | Garito et al. | 6,632,193 B1 | 10/2003 | Davison et al. |
| 6,004,333 A | 12/1999 | Sheffield et al. | 6,652,514 B2 | 11/2003 | Ellman et al. |
| 6,004,335 A | 12/1999 | Vaitekunas et al. | 6,662,053 B2 | 12/2003 | Borkan |
| 6,010,499 A | 1/2000 | Cobb | 6,669,691 B1 | 12/2003 | Taimisto |
| 6,022,347 A | 2/2000 | Lindenmeier et al. | 6,685,701 B2 | 2/2004 | Orszulak et al. |
| 6,045,564 A | 4/2000 | Walen | 6,685,704 B2 | 2/2004 | Greep |
| 6,063,050 A | 5/2000 | Manna et al. | 6,702,812 B2 | 3/2004 | Cosmescu |
| 6,068,603 A | 5/2000 | Suzuki | 6,710,546 B2 | 3/2004 | Crenshaw |
| 6,068,627 A | 5/2000 | Orszulak et al. | 6,712,813 B2 | 3/2004 | Ellman et al. |
| 6,070,444 A | 6/2000 | Lontine et al. | 6,719,746 B2 | 4/2004 | Blanco |
| 6,071,281 A | 6/2000 | Burnside et al. | 6,740,079 B1 | 5/2004 | Eggers et al. |
| 6,074,386 A | 6/2000 | Goble et al. | 6,747,218 B2 | 6/2004 | Huseman et al. |
| 6,074,387 A | 6/2000 | Heim et al. | D493,530 S | 7/2004 | Reschke |
| 6,086,544 A | 7/2000 | Hibner et al. | D493,888 S | 8/2004 | Reschke |
| 6,090,123 A | 7/2000 | Culp et al. | D494,270 S | 8/2004 | Reschke |
| 6,099,525 A | 8/2000 | Cosmescu | D495,051 S | 8/2004 | Reschke |
| 6,117,134 A | 9/2000 | Cunningham et al. | D495,052 S | 8/2004 | Reschke |
| 6,139,547 A | 10/2000 | Lontine et al. | 6,794,929 B2 | 9/2004 | Pelly |
| D433,752 S | 11/2000 | Saravia | 6,830,569 B2 | 12/2004 | Thompson et al. |
| 6,142,995 A | 11/2000 | Cosmescu | 6,840,948 B2 | 1/2005 | Albrecht et al. |
| 6,146,353 A | 11/2000 | Platt, Jr. | 6,855,140 B2 | 2/2005 | Albrecht et al. |
| 6,149,648 A | 11/2000 | Cosmescu | 6,902,536 B2 | 6/2005 | Manna et al. |
| 6,156,035 A | 12/2000 | Songer | 6,905,496 B1 | 6/2005 | Ellman et al. |
| 6,197,024 B1 | 3/2001 | Sullivan | 6,923,804 B2 | 8/2005 | Eggers et al. |

| | | |
|---|---|---|
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| D535,396 S | 1/2007 | Reschke et al. |
| 7,156,842 B2 | 1/2007 | Sartor et al. |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1* | 2/2003 | Altshuler et al. .............. 606/9 |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki et al. |
| 2004/0034346 A1 | 2/2004 | Stern et al. |
| 2004/0054370 A1 | 3/2004 | Given |
| 2004/0092927 A1 | 5/2004 | Podhajsky et al. |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0230262 A1 | 11/2004 | Sartor et al. |
| 2004/0236323 A1 | 11/2004 | Schoenman et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0107782 A1 | 5/2005 | Reschke |
| 2005/0113817 A1 | 5/2005 | Isaacson et al. |
| 2005/0113818 A1 | 5/2005 | Sartor et al. |
| 2005/0113823 A1 | 5/2005 | Reschke et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0058783 A1* | 3/2006 | Buchman, III ................ 606/42 |
| 2006/0178667 A1 | 8/2006 | Sartor et al. |
| 2007/0049926 A1 | 3/2007 | Sartor |
| 2007/0093810 A1 | 4/2007 | Sartor |

FOREIGN PATENT DOCUMENTS

| | | |
|---|---|---|
| DE | 24 60 481 A1 | 6/1976 |
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1645234 | 4/2006 |
| EP | 1656900 | 5/2006 |
| EP | 1852078 | 11/2007 |
| FR | 2798579 | 3/1923 |
| FR | 2235669 | 1/1975 |
| WO | WO94/20032 | 9/1994 |
| WO | WO 96/39086 | 12/1996 |
| WO | WO 98/43264 | 10/1998 |
| WO | WO01/64122 | 9/2001 |
| WO | WO 02/47568 A1 | 6/2002 |
| WO | WO 2004/010883 A1 | 2/2004 |
| WO | WO 2004/045436 | 6/2004 |
| WO | WO 2004/073753 A2 | 9/2004 |
| WO | WO 2005/060849 A1 | 7/2005 |

OTHER PUBLICATIONS

International Search Report from PCT/US04/04685; Aug. 6, 2004.
International Search Report from EP/0401/5980; Sep. 30, 2004.
International Search Report from PCT/US03/22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 04711864.1 dated Dec. 11, 2006.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).
International Search Report EP 08 002 357 dated Jun. 30, 2008.
European Search Report from Application EP 07009028 dated Jul. 16, 2007.
International Search Report EP 06 005 540.7 dated Sep. 24, 2007.

* cited by examiner

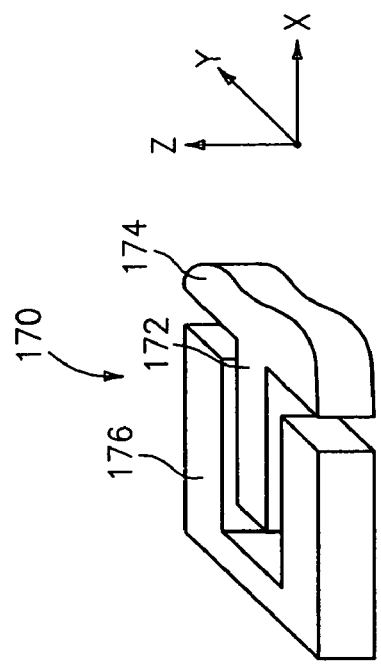
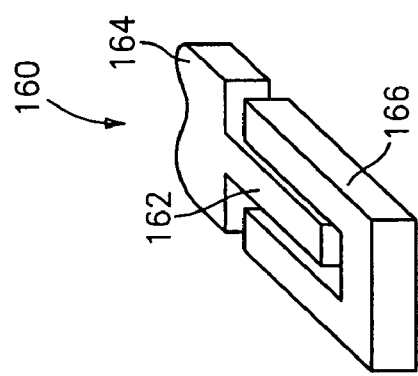
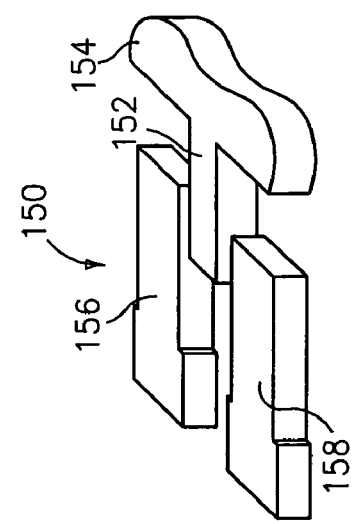

MOTION DETECTOR FOR CONTROLLING ELECTROSURGICAL OUTPUT

CROSS-REFERENCE TO RELATED APPLICATIONS

The present application is a continuation of U.S. application Ser. No. 10/781,084, filed Feb. 17, 2004, now U.S. Pat. No. 7,235,072, which claims the benefit of and priority to U.S. Provisional Patent Application No. 60/448,520, filed on Feb. 20, 2003, and U.S. Provisional Patent Application No. 60/533,695, filed Jan. 1, 2004, the entire contents of which are incorporated herein by reference.

BACKGROUND

1. Technical Field

The present disclosure relates generally to an electrosurgical instrument and, more particularly, to an electrosurgical pencil having a motion detector for controlling the electrosurgical output thereof.

2. Background of Related Art

Electrosurgical instruments have become widely used by surgeons in recent years. Accordingly, a need has developed for equipment that is easy to handle, is easy to operate, and is reliable and safe. By and large, most surgical instruments typically include a variety of hand-held pencils, e.g., electrosurgical pencils, forceps, scissors and the like, and electrosurgical pencils, which transfer energy to a tissue site. The electrosurgical energy is initially transmitted from an electrosurgical generator to an active electrode which, in turn, transmits the electrosurgical energy to the tissue. In a monopolar system, a return electrode pad is positioned under the patient to complete the electrical path to the electrosurgical generator. A smaller return electrode is positioned in bodily contact with or immediately adjacent to the surgical site in a bipolar system configuration.

For the purposes herein, the term electrosurgical fulguration includes the application of an electric spark to biological tissue, for example, human flesh or the tissue of internal organs, without significant cutting. The spark is produced by bursts of radio-frequency electrical energy generated from an appropriate electrosurgical generator. Generally, electrosurgical fulguration is used to dehydrate, shrink, necrose or char tissue. As a result, electrosurgical fulguration instruments are primarily used to stop bleeding and oozing of various surgical fluids. These operations are generally embraced by the term "coagulation." Meanwhile, electrosurgical "cutting" includes the use of the applied electric spark to tissue which produces a cutting effect. By contrast, electrosurgical "sealing" includes utilizing a unique combination of electrosurgical energy, pressure and gap distance between electrodes to melt the tissue collagen into a fused mass.

It is known that certain electrosurgical waveforms are preferred for different surgical effects. For example, a continuous (i.e., steady) sinusoidal waveform is preferred to enhance the cutting effect of the electrosurgical blade in an electrosurgical pencil or enhance the cooperative effect of the two opposing jaw members. A series of discontinuous, high energy electrosurgical pulses are preferred to enhance the coagulation of biological tissue. Other types of electrosurgical waveforms are preferred for electrosurgical "blending", "shorting" or fusing tissue. As can be appreciated, these waveforms are typically regulated by the generator and are generally dependent upon the desired mode of operation manually selected by the surgeon at the onset (or during) the operation.

As used herein, the term "electrosurgical pencil" is intended to include instruments which have a handpiece which is attached to an active electrode and are used to coagulate, cut, and seal tissue. The pencil may be operated by a hand-switch (in the form of a depressible button provided on the handpiece itself) or a foot-switch (in the form of a depressible pedal operatively connected to the handpiece). The active electrode is an electrically conducting element which is usually elongated and may be in the form of a thin flat blade with a pointed or rounded distal end. Typically, electrodes of this sort are known in the art as "blade" type. Alternatively, the active electrode may include an elongated narrow cylindrical needle which is solid or hollow with a flat, rounded, pointed or slanted distal end. Typically, electrodes of this sort are known in the art as "loop" or "snare", "needle" or "ball" type.

As mentioned above, the handpiece of the pencil is connected to a suitable electrosurgical source (e.g., generator) which supplies the electrosurgical energy necessary to the conductive element of the electrosurgical pencil. In general, when an operation is performed on a patient with an electrosurgical pencil, energy from the electrosurgical generator is conducted through the active electrode to the tissue at the site of the operation and then through the patient to a return electrode. The return electrode is typically placed at a convenient place on the patient's body and is attached to the generator by a return cable.

During the operation, the surgeon depresses the hand-switch or foot-switch to activate the electrosurgical pencil. Then, depending on the level of radio-frequency electrosurgical energy desired for the particular surgical effect, the surgeon manually adjusts the power level on the electrosurgical generator by, for example, rotating a dial on the electrosurgical instrument. Recently, electrosurgical pencils have been developed which vary the level of electrosurgical energy delivered depending on the amount of drag sensed by the active electrode or by the degree the hand-switch has been depressed by the surgeon. Examples of some of these instruments are described in commonly assigned U.S. Provisional Application Nos. 60/398,620 filed Jul. 25, 2002 and 60/424,352 filed Nov. 5, 2002, the entire contents of which are hereby incorporated by reference.

Accordingly, a need exists for an electrosurgical pencil which is activated without the use of hand-switches or foot-switches and which can automatically control the electrosurgical output from the electrosurgical generator without manual intervention by the surgeon.

SUMMARY

An electrosurgical instrument having a movement sensing device for controlling the electrosurgical output thereof, is disclosed. In one aspect of the present disclosure, the electrosurgical instrument includes an elongated housing, an electrically conductive element supported within the housing and extending distally from the housing, the electrically conductive element being connectable to a source of electrosurgical energy, and a sensor disposed within the housing and in electrical connection with the electrosurgical generator. The sensor detects movement of the electrically conductive element and communicates a signal to the electrosurgical generator relating to the movement of the electrically conductive element. The source of electrosurgical energy supplies electrosurgical energy in response to the signal communicated from the sensor.

It is envisioned that the sensor for detecting movement of the electrically conductive element is at least one of force-sensing transducers, accelerometers, optical positioning systems, radiofrequency positioning systems, ultrasonic positioning systems and magnetic field positioning systems.

Preferably, the electrically conductive element includes a longitudinal axis defined therethrough and the sensor detects at least one of a axial movement of the electrically conductive element along the longitudinal axis, a transverse movement across the longitudinal axis of the electrically conductive element, and a rotational movement about the longitudinal axis of the electrically conductive element. In one embodiment it is envisioned that the source of electrosurgical energy transmits a dissecting RF energy output in response to the detection of axial movement of the electrically conductive element along the longitudinal axis. In another embodiment it is envisioned that the source of electrosurgical energy transmits a hemostatic RF energy output in response to the detection of transverse movement of the electrically conductive element across the longitudinal axis.

It is envisioned that the sensor is at least one of a differential parallel plate accelerometer, a balanced interdigitated comb-finger accelerometer, an offset interdigitated comb-finger accelerometer and a film-type accelerometer. Preferably, the sensor includes a first accelerometer for detecting a movement of the electrically conductive element in an axial direction along the longitudinal axis and a second accelerometer for detecting movement of the electrically conductive element in a transverse direction across the longitudinal axis. It is also envisioned that the sensor may include at least one piezoelectric film.

In one embodiment it is contemplated that the first accelerometer is configured and adapted to transmit an output signal to the electrosurgical energy source corresponding to the axial movement of the electrically conductive element, and the second accelerometer is configured and adapted to transmit an output signal to the electrosurgical energy source corresponding to the transverse movement of the electrically conductive element. Preferably, each of the first and second accelerometers is at least one of a differential parallel plate accelerometer, a balanced interdigitated comb-finger accelerometer, an offset interdigitated comb-finger accelerometer and a film-type accelerometer.

In certain embodiments it is envisioned that the source of electrosurgical energy ceases supplying electrosurgical energy when the sensor does not detect a movement of the electrosurgical pencil for a predetermined period of time and/or does not detect a movement of the electrosurgical pencil above a predetermined threshold level of movement.

It is further envisioned that in certain embodiments the source of electrosurgical energy resumes supplying electrosurgical energy when the sensor detects a movement of the electrosurgical pencil following the predetermined period of time and/or detects a movement of the electrosurgical pencil above the predetermined threshold level of movement.

These and other objects will be more clearly illustrated below by the description of the drawings and the detailed description of the preferred embodiments.

BRIEF DESCRIPTION OF THE DRAWINGS

The accompanying drawings, which are incorporated and constitute a part of this specification, illustrate embodiments of the disclosure and, together with a general description of the disclosure given above, and the detailed description of the embodiments given below, serve to explain the principles of the disclosure.

FIGS. 2A-2C illustrate three embodiments of accelerometers suitable for in-plane sensing or forcing;

DETAILED DESCRIPTION

Figure 1:
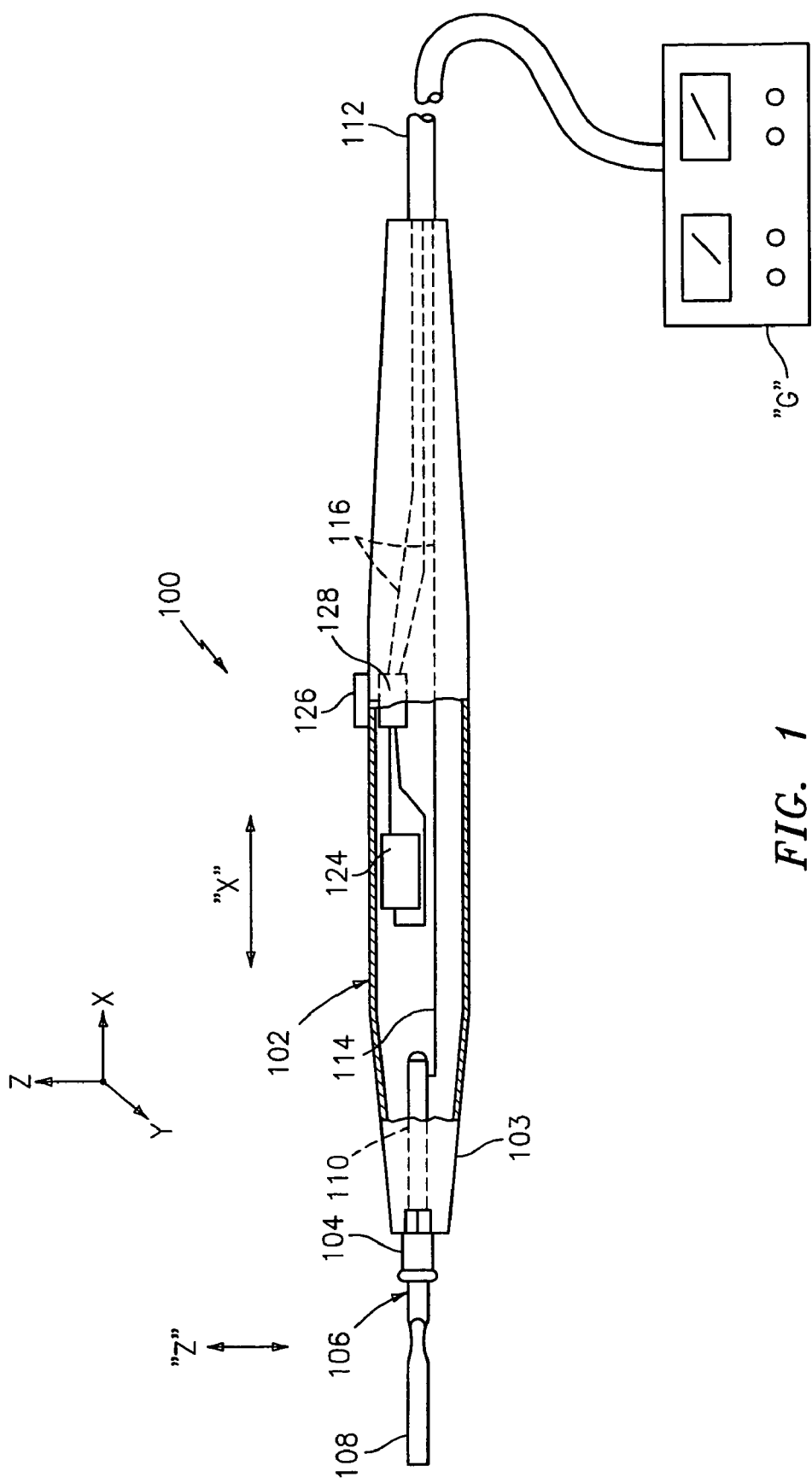
FIG. 1 is a partially broken away side, elevational view of an embodiment of the electrosurgical pencil in accordance with the present disclosure.

Embodiments of the presently disclosed electrosurgical pencil will now be described in detail with reference to the drawing figures wherein like reference numerals identify similar or identical elements. In the drawings, and in the description which follows, as is traditional, the term "proximal" will refer to the end of the electrosurgical pencil which is closest to the operator, while the term "distal" will refer to the end of the electrosurgical pencil which is furthest from the operator.

Acceleration is a physical quality which often must be sensed or measured. Acceleration is defined as the rate of change of velocity with respect to time. For example, acceleration is often sensed to measure force or mass, or to operate some kind of control system. At the center of any acceleration measurement is an acceleration-sensing element, or force-sensing transducer. The transducer is often mechanical or electromechanical element (e.g., a piezo-electric transducer, a piezo-resistive transducer or a strain gauge) which is typically interfaced with an electrical signal or electrical circuits for providing a useful output signal to a generator, computer or other surgical console. Exemplary transducers are described in U.S. Pat. Nos. 5,367,217, 5,339,698, and 5,331,242, the entire contents of which are incorporated herein by reference. An accelerometer is defined as an instrument which measures acceleration or gravitational force capable of imparting acceleration. Another type of force-sensing transducer is an accelerometer. Exemplary accelerometers are described in U.S. Pat. Nos. 5,594,170, 5,501,103, 5,379,639, 5,377,545, 5,456,111, 5,456,110, and 5,005,413, the entire contents of which are incorporated herein by reference.

Several types of accelerometers are known. A first type of accelerometer incorporates a bulk-micromachined silicon mass suspended by silicon beams, wherein ion-implanted piezo-resistors on the suspension beams sense the motion of the mass. A second type of accelerometer utilizes a change in capacitance to detect movement of the mass. A third type of accelerometer detects acceleration by measuring a change in a structure's resonant frequency as a result of a shift in the physical load of the structure. It is envisioned that the accelerometers can include a piezoelectric film sandwiched into a weighted printed flex circuit. It is also envisioned that at least one resistive flex circuit could be used to detect the position and/or orientation of the surgical instrument rather than acceleration.

Turning now to FIG. 1, there is set forth a partially broken away side, elevational view of an electrosurgical pencil constructed in accordance with an embodiment of the present disclosure and generally referenced by numeral 100. While the following description will be directed towards electrosurgical pencils, it is envisioned that the features and concepts of the present disclosure can be applied to other electrosurgical instruments, e.g., dissectors, ablation instruments, probes, etc. Electrosurgical pencil 100 includes an elongated housing 102 configured and adapted to support a blade receptacle 104 at a distal end 103 thereof which, in turn, receives an electrocautery blade 106 therein. A distal end 108 of blade 106 extends distally from receptacle 104 while a proximal end 110 of blade 106 is retained within the distal end 103 of housing 102. Preferably, electrocautery blade 106 is fabricated from a conductive material, e.g., stainless steel or aluminum or is coated with an electrically conductive material.

As shown, electrosurgical pencil 100 is coupled to a conventional electrosurgical generator "G" via a cable 112. Cable 112 includes a transmission wire 114 which electrically interconnects electrosurgical generator "G" with proximal end 110 of electrocautery blade 106. Cable 112 further includes a control loop 116 which electrically interconnects a movement sensing device 124 (e.g., an accelerometer), supported within housing 102, with electrosurgical generator "G".

By way of example only, electrosurgical generator "G" may be any one of the following, or equivalents thereof: the "FORCE FX", "FORCE 2" or "FORCE 4" generators manufactured by Valleylab, Inc., a division of Tyco Healthcare, LP, Boulder, Colo. Preferably, the energy output of electrosurgical generator "G" can be variable in order to provide appropriate electrosurgical signals for tissue cutting (e.g., 1 to 300 watts) and appropriate electrosurgical signals for tissue coagulation (e.g., 1 to 120 watts). One example of a suitable electrosurgical generator "G" is disclosed in commonly-assigned U.S. Pat. No. 6,068,627 to Orszulak, et al., the entire contents of which are incorporated herein by reference. The electrosurgical generator disclosed in the '627 patent includes, inter alia, an identifying circuit and a switch therein. In general, the identification circuit is responsive to the information received from a generator and transmits a verification signal back to the generator. Meanwhile, the switch is connected to the identifying circuit and is responsive to signaling received from the identifying circuit.

Electrosurgical pencil 100 further includes an activation button 126 supported on an outer surface of housing 102. Activation button 126 is operable to control a depressible switch 128 which is used to control the delivery of electrical energy transmitted to electrocautery blade 106.

Turning back to FIG. 1, as mentioned above, electrosurgical pencil 100 includes an accelerometer 124 which is supported within housing 102. Accelerometer 124 is operatively connected to generator "G" which, in turn, controls and transmits an appropriate amount of electrosurgical energy to electrocautery blade 106 and/or controls the waveform output from electrosurgical generator "G".

In use, the surgeon activates electrosurgical pencil 100 by depressing activation button 126 thereby allowing electrical energy to be transmitted to electrocautery blade 106. With activation button 126 depressed, as the surgeon moves electrosurgical pencil 100 repeatedly along the X axis (i.e., in a stab-like motion), as indicated by double-headed arrow "X" in FIG. 1, accelerometer 124 transmits a corresponding signal, through control loop 116, to generator "G". Generator "G" then interprets the signal received from accelerometer 124 and, in turn, transmits a corresponding dissecting electrosurgical energy output (i.e., specific power and waveform associated with dissecting), via transmission wire 114, to electrocautery blade 106.

On the other hand, if the surgeon moves electrosurgical pencil 100 in a direction orthogonal to the X axis, for example, as indicated by double-headed arrow "Z" in FIG. 1, accelerator 124 transmits a corresponding signal, through control loop 116, to generator "G". Generator "G" then interprets the orthogonal signal received from accelerometer 124 and, in turn, transmits a hemostatic electrosurgical energy output (i.e., specific power and waveform associated with hemostasis), via transmission wire 114, to electrocautery blade 106.

Accordingly, the electrosurgical pencil of the present disclosure will enable a surgeon to control the type of output and/or the amount of energy delivered to electrocautery blade 106 by simply moving electrosurgical pencil in a particular pattern or direction. In this manner, the surgeon does not have to depress any buttons or switches which are disposed on the electrosurgical pencil 100 in order to produce either a dissecting or hemostasis energy output in electrocautery blade 106. As can be appreciated, the surgeon does not have to adjust dials or switches on generator "G" in order to produce either the dissecting or hemostasis energy output in electrocautery blade 106.

Accelerometers suitable for position sensing or electrostatic forcing may be formed with fixed and movable electrodes in many configurations. Several embodiments of accelerometers having in-plane motion sensitivity are shown in FIG. 2, along with an orthogonal coordinate system. In particular, as seen in FIGS. 2A-2C, a differential parallel plate accelerometer is shown generally as 150. Differential parallel plate accelerometer 150 includes an electrode 152, attached to a proof mass 154, which is movable along the Y-axis thereby changing the gap between movable electrode 152 and fixed electrodes 156 and 158. Motion of movable electrode 152, along the Y-axis, causes opposite changes in capacitance formed by electrode pair 152, 156 and 152, 158. In FIG. 2B, a balanced, interdigitated comb-finger accelerometer is shown generally as 160.

Balanced, interdigitated comb-finger accelerometer 160 includes an electrode 162, attached to a proof mass 164, which is movable along the Y-axis thereby changing the overlap area between movable electrode 162 and a fixed wrap-around electrode 166. In FIG. 2C, an offset, interdigitated comb-finger accelerometer is shown generally as 170. Offset, interdigitated comb-finger accelerometer 170 includes an electrode 172, attached to a proof mass 174, which is movable along the Y-axis thereby changing gaps between movable electrode 172 and a fixed wrap-around electrode 176.

While a single accelerometer 124 which can measure changes in the acceleration of electrosurgical pencil 100 in the axial (i.e., X-direction), lateral (i.e., Y-direction) and vertical (i.e., Z-direction) directions is preferred, it is envisioned that a pair of identical accelerometers or different accelerometers (i.e., accelerometers 150, 160 and 170), as shown in FIGS. 2A-2C, can be used. For example, a first accelerometer, such as, offset interdigitated comb-finger accelerometer 170, can be mounted within electrosurgical pencil 100 such that a displacement of movable electrode 172 in the Y-direction results in the transmission of dissecting electrosurgical energy by generator "G" to electrocautery blade 106 while a second accelerator, such as, another offset interdigitated comb-finger accelerometer 170, can be mounted within electrosurgical pencil 100, orthogonal to the first accelerometer, such that a displacement of movable electrode 172 in the X-direction results in transmission of hemostatic electrosurgical energy by generator "G" to electrocautery blade 106.

It is envisioned that any combination of accelerometers can be provided in electrosurgical pencil 100 in any number of orientations to measure changes in acceleration in any number of directions including rotational acceleration (Y-direction and Z-direction). It is also envisioned that any combination of accelerations in the X-direction, Y-direction and Z-direction can also be detected, measured and calculated to effect the electrosurgical output from Generator "G".

In addition to accelerometers, it is envisioned that many other types of sensors for detecting movement of electrocautery blade 106 can be provided. Other types of force-sensing transducers may be used. Other types, including and not limited to, optical positioning systems, radiofrequency positioning systems, ultrasonic positioning systems and magnetic field positioning systems may be used.

While an active electrode in the form of a blade has been shown and described, it is envisioned that any type of tip can be used as the active electrode of electrosurgical pencil 100. For example, the active electrode can be an elongated narrow cylindrical needle which is solid or hollow with a flat, rounded, pointed or slanted distal end.

It is further envisioned that the amount of time required for the transmission of electrosurgical energy from the generator "G" to the electrocautery blade 106, in response to an output signal received from the accelerometer 124 can be adjusted based on the degree of responsiveness desired by the surgeon. For example, a relatively shorter response time would be considered more responsive than a relatively longer response time.

In addition, it is envisioned that the accelerometer 124 be provided with motion detection algorithms which transmit energy cut-off signals to generator "G" if electrosurgical pencil 100 is held motionless or laid down for an extended period of time. It is contemplated that the sensitivity to activation of electrosurgical pencil 100, in response to an axial, vertical or transverse movement, may be decreased as time lapses from the last time that electrosurgical pencil 100 was used. As such, electrosurgical pencil 100 would be less likely to be inadvertently activated as more time elapses. In addition, the ability to disable the electrosurgical pencil 100 when not in use improves the clinical safety of the device. The motion detection algorithm effectively creates a "virtual holster" which keeps electrosurgical pencil 100 from being inadvertently activated.

Figure 3:
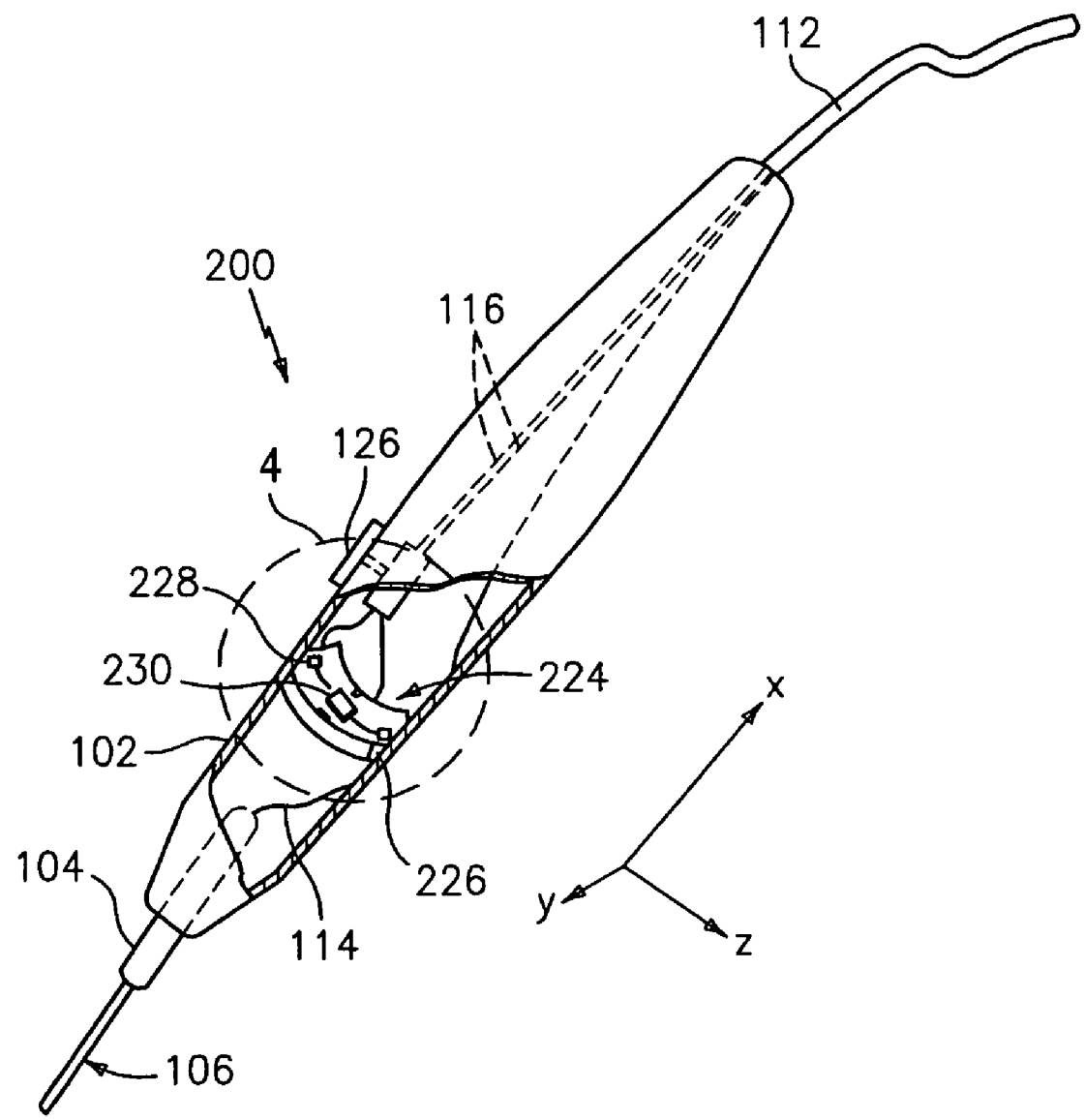
FIG. 3 is a partially broken away perspective view of an electrosurgical pencil in accordance with another embodiment of the present disclosure.
Figure 4:
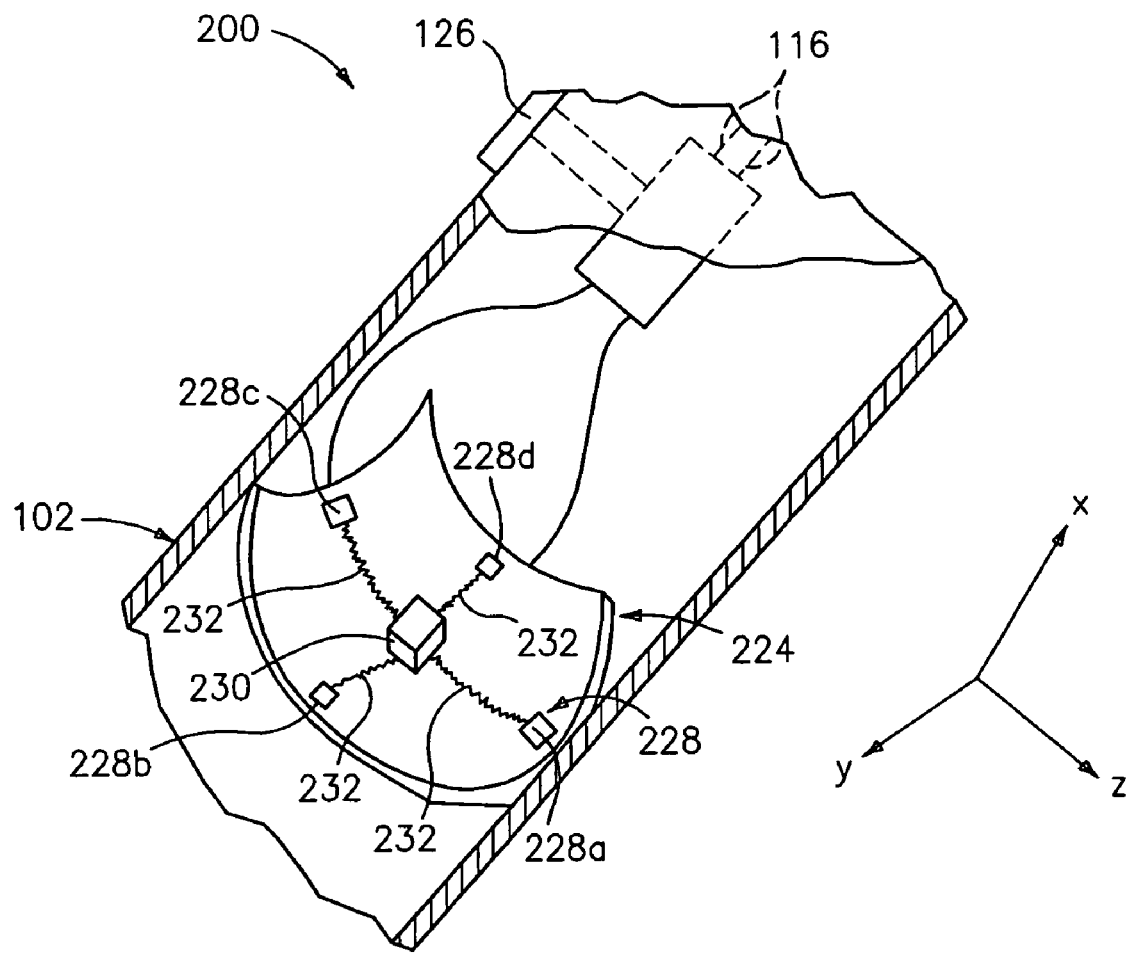
FIG. 4 is an enlarged perspective view of the indicated area of FIG. 3.

Turning now to FIGS. 3 and 4, there is set forth a partially broken away perspective view of an electrosurgical pencil constructed in accordance with another embodiment of the present disclosure and generally referenced by numeral 200. Electrosurgical pencil 200 is similar to electrosurgical pencil 100 and will only be discussed in detail to the extent necessary to identify differences in construction and operation.

As seen in FIGS. 3 and 4, electrosurgical pencil 200 includes a film-type accelerometer or sensor 224 supported in housing 102. Sensor 224 is preferably includes substrate 226 fabricated from an elastomeric material. Sensor 224 further includes an array of electrodes 228 (in the interest of clarity only four electrodes 228a-228d have been shown) positioned around the periphery of substrate 226. Sensor 224 further includes a proof mass 230 electrically connected to each electrode 228 via electrical leads 232. Proof mass 230 is movable in any direction along axes X, Y and Z thereby changing the gap distance between itself and electrodes 228 and the resistance through leads 232.

Accordingly, motion of proof mass 230, along the X, Y and/or Z axis results in transmission of a particular signal, through control loop 116, to generator "G" (see FIG. 1). Generator "G" then interprets the particular signal received from sensor 224 and, in turn, transmits a corresponding distinct electrosurgical energy output (i.e., specific power and/or waveform), via transmission wire 114, to electrocautery blade 106.

For example, with activation button 126 depressed, movement by the surgeon of electrosurgical pencil 200 is directions along the X axis (i.e., in a stab-like motion), causes sensor 224 to transmit a first characteristic signal to generator "G". Generator "G" interprets the first characteristic signal and, in turn, transmits a corresponding dissecting electrosurgical energy output (i.e., a specific power and a specific waveform associated with dissecting), to electrocautery blade 106.

In a further example, with activation button 126 depressed, movement by the surgeon of electrosurgical pencil 200 in directions transverse to the X axis, such as, for example, along the Y and/or Z axes, causes sensor 224 to transmit a second characteristic signal to generator "G". Generator "G" interprets the second characteristic signal and, in turn, transmits a corresponding hemostatic electrosurgical energy output (i.e., a specific power and a specific waveform associated with hemostasis), to electrocautery blade 106.

It is envisioned that substrate 226 has a concave-like configuration. In this manner, when the surgeon holds electrosurgical pencil 200 still, proof mass 230 will have a tendency to return to the bottom of substrate 226 and effectively reset itself automatically. In other words, a concave-like substrate 226 can be self-centering and thus provide electrosurgical pencil 200 with a self-resetting capability. It is also envisioned that other shapes may be used.

Accordingly, the electrosurgical energy output of electrosurgical pencils 100, 200 will be controlled by the natural movements of the surgeon's hand and no specific thought is required to change the corresponding energy output from a "dissecting" setting to a "hemostatic" setting and vice-a-versa.

It is envisioned that when electrosurgical pencil 100, 200 is held motionless for a predetermined amount of time and/or below a predetermined threshold level of movement (i.e., accelerometer 124 and/or sensor 224 do not sense movement of electrosurgical pencil 100 or 200 for a predetermined period of time and/or sense movement which is below a predetermined threshold level), electrosurgical generator "G" does not transmit electrosurgical energy to the electrocautery blade. It is further envisioned that the sensitivity of electrosurgical pencil 100 or 200 can be increased and/or decreased by adjusting the threshold levels of time and movement accordingly.

It is further envisioned that electrosurgical generator "G" begins and/or resumes supplying electrosurgical energy to the electrocautery blade when accelerometer 124 and/or sensor 224 detects a movement of electrosurgical pencil 100 or 200 after the predetermined period of time has elapsed and/or after the predetermined threshold level has been surpassed.

From the foregoing and with reference to the various figure drawings, those skilled in the art will appreciate that certain modifications can also be made to the present disclosure without departing from the scope of the present disclosure. For example, embodiments of the present disclosure include an electrosurgical pencil having a button for controlling the electrosurgical energy output, in addition to the sensor or sensors discussed above. While embodiments of electrosurgical instruments according to the present disclosure have been described herein, it is not intended that the disclosure be limited there and that the above description should be construed as merely exemplifications of preferred embodiments.

What is claimed is:

1. An electrosurgical instrument, comprising:
a housing;
an electrically conductive element at least partially supported in the housing and extending therefrom, the electrically conductive element adapted to connect to a source of electrosurgical energy;
a motion sensor disposed within the housing and adapted to electrically connect to the source of electrosurgical energy, the motion sensor operable to detect a movement of the electrosurgical instrument in a plurality of directions; and
wherein the motion sensor is operable to transmit a signal to the source of electrosurgical energy for de-activation of a transmission of energy from the source of electrosurgical energy when the motion sensor does not detect movement of the electrosurgical instrument for a period of time at least equal to a predetermined period of time, wherein the electrically conductive element includes a longitudinal axis defined therethrough and the motion sensor is operable to detect at least one of an axial movement of the electrosurgical instrument relative to the longitudinal axis, a transverse movement of the electrosurgical instrument relative to the longitudinal axis, and a rotational movement of the electrosurgical instrument about the longitudinal axis, wherein the motion sensor includes:
- a first accelerometer operable to detect the axial movement and transmit a first signal to the source of electrosurgical energy corresponding to the axial movement; and
- a second accelerometer operable to detect the transverse movement transmit a second signal to the source of electrosurgical energy corresponding to the transverse movement.

2. The electrosurgical instrument according to claim 1, wherein the motion sensor is at least one of an accelerometer, an optical positioning system, a radiofrequency positioning system, an ultrasonic positioning system, a differential parallel plate accelerometer, a balanced interdigitated comb-finger accelerometer, an offset interdigitated comb-finger accelerometer, and a film-type accelerometer.

3. The electrosurgical instrument according to claim 1, wherein each of the first and second accelerometers is at least one of a differential parallel plate accelerometer, a balanced interdigitated comb-finger accelerometer, an offset interdigitated comb-finger accelerometer, a film-type accelerometer, and at least one piezoelectric film motion detector.

4. An electrosurgical instrument, comprising:
   a housing;
   an electrically conductive element at least partially supported in the housing and extending therefrom, the electrically conductive element adapted to connect to a source of electrosurgical energy; and
   a sensor disposed within the housing and adapted to electrically connect with the source of electrosurgical energy, the sensor operable to detect a movement of the electrosurgical instrument as the electrosurgical instrument is moved in free space, wherein the sensor is operable to transmit a signal to the source of electrosurgical energy for controlling a transmission of energy from the source of electrosurgical energy based on the movement,
   wherein the electrically conductive element includes a longitudinal axis defined therethrough and the motion sensor is operable to detect at least one of an axial movement of the electrosurgical instrument relative to the longitudinal axis, a transverse movement of the electrosurgical instrument relative to the longitudinal axis, and a rotational movement of the electrosurgical instrument about the longitudinal axis,
   wherein the motion sensor includes:
   - a first accelerometer operable to detect the axial movement and transmit a first signal to the source of electrosurgical energy corresponding to the axial movement; and
   - a second accelerometer operable to detect the transverse movement transmit a second signal to the source of electrosurgical energy corresponding to the transverse movement.

5. The electrosurgical instrument according to claim 4, wherein the sensor is at least one of an accelerometer, an optical positioning system, a radiofrequency positioning system, an ultrasonic positioning system, a differential parallel plate accelerometer, a balanced interdigitated comb-finger accelerometer, an offset interdigitated comb-finger accelerometer, and a film-type accelerometer.

6. The electrosurgical instrument according to claim 4, wherein the signal is operable to cause the source of electrosurgical energy to transmit a dissecting RF energy output in response to the detection of the axial movement.

7. The electrosurgical instrument according to claim 4, wherein the signal is operable to cause the source of electrosurgical energy to transmit a hemostatic RF energy output in response to the detection of the transverse movement.

8. The electrosurgical instrument according to claim 4, wherein the signal is operable to cause the source of electrosurgical energy to reduce the supply of electrosurgical energy when the sensor fails to detect at least one of:
   movement of the electrosurgical instrument for a predetermined period of time; and
   movement of the electrosurgical instrument above a predetermined threshold level of movement.

9. The electrosurgical instrument according to claim 7, wherein the signal is operable to cause the source of electrosurgical energy to increase the supply of electrosurgical energy when the sensor detects at least one of:
   movement of the electrosurgical instrument following the predetermined period of time; and
   movement of the electrosurgical instrument above the predetermined threshold level of movement.

10. An electrosurgical system, comprising:
    a source of electrosurgical energy;
    an electrosurgical instrument coupled to the source of electrosurgical energy, the electrosurgical instrument including:
    an elongated housing;
    an electrically conductive element at least partially supported in the housing and extending therefrom, the electrically conductive element connectable to the source of electrosurgical energy and having a longitudinal axis defined therethrough; and
    a motion sensor disposed within the housing and in electrical connection with the source of electrosurgical energy, the motion sensor operable to detect a movement of the electrosurgical instrument in a plurality of directions, wherein the motion sensor is operable to transmit a signal to the source of electrosurgical energy for de-activation of a transmission of energy from the source of electrosurgical energy when the motion sensor does not detect movement of the electrosurgical instrument for a period of time at least equal to a predetermined period of time,
    wherein the source of electrosurgical energy is operable to transmit a dissecting RF energy output in response to the detection of an axial movement of the electrosurgical instrument along the longitudinal axis,
    wherein the source of electrosurgical energy is operable to transmit a hemostatic RF energy output in response to the detection of a transverse movement of the electrosurgical instrument across the longitudinal axis.

* * * * *